March 15, 1960 F. W. ANDERSON Plant Pat. 1,921
NECTARINE TREE
Filed Aug. 10, 1959
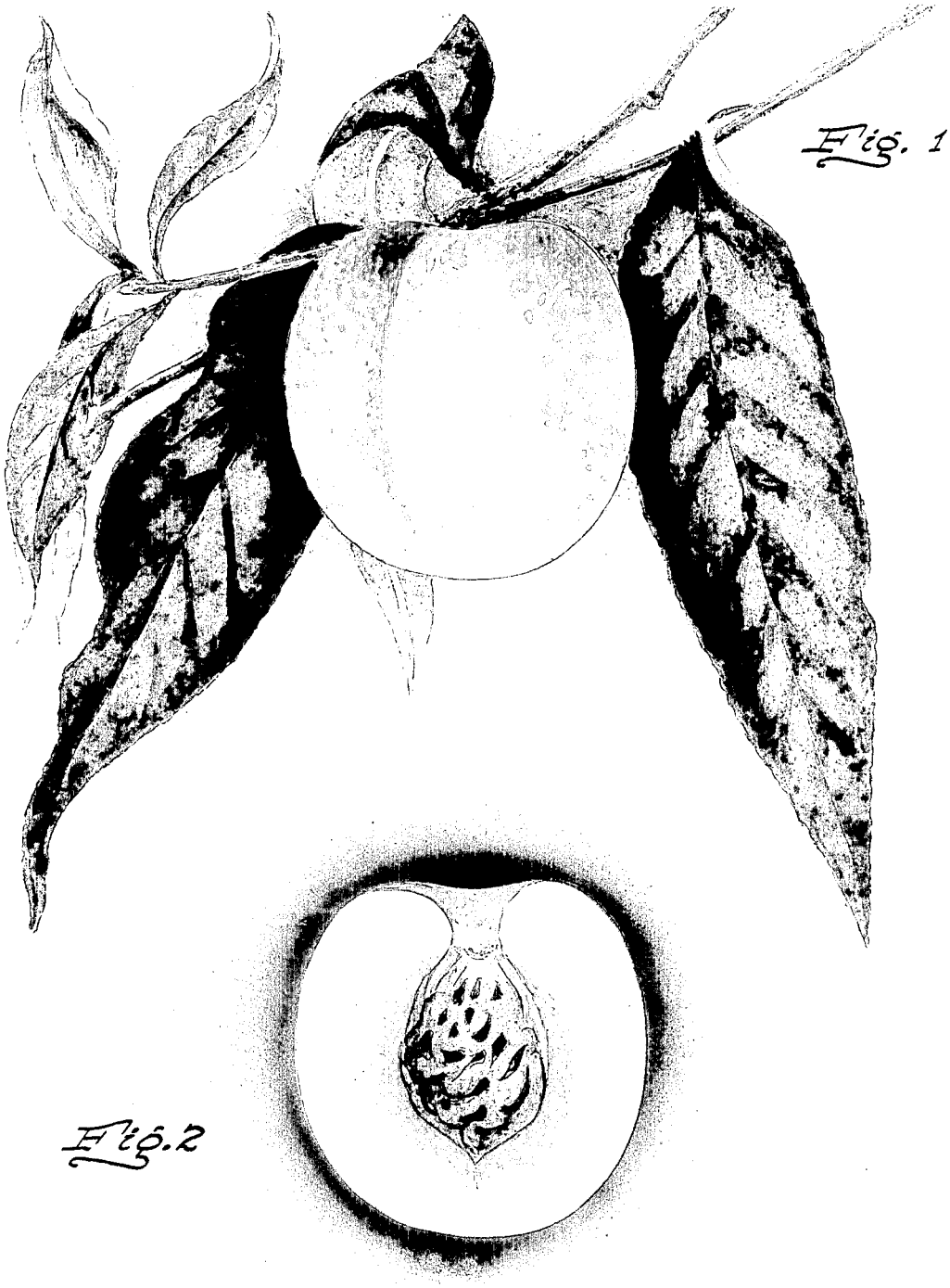
WITNESS
Addison E. Avery
INVENTOR
Frederic W. Anderson
Webster & Webster
ATTYS.

United States Patent Office

Plant Pat. 1,921
Patented Mar. 15, 1960

1,921

NECTARINE TREE

Frederic W. Anderson, Merced, Calif., assignor to Stark Bros. Nurseries and Orchards Co., Louisiana, Mo., a corporation of Missouri Application August 10, 1959, Serial No. 832,872

1 Claim. (Cl. 47—62)

The present invention relates to a new and distinct variety of nectarine tree which bears yellow-fleshed, freestone fruit having yellow skin mottled with red; the variety being of the type embraced by group 111 of the classification by Caillavet and Souty, Monographie des Principales Variétés de Pêchers, 1950 edition, page 46.

As compared with the Sun Grand (United States Plant Patent No. 974)—which, at present, is the most extensively commercially grown freestone nectarine in California—the present variety has leaves with reniform instead of globose glands, and bears fruit which is larger in size, ripens approximately ten days earlier, and has less red exterior color.

The variety was originated by me in my experimental orchard located near Merced, California, and is a cross between the Late Le Grand nectarine (United States Plant Patent No. 1,035) and the Star Grand nectarine (United States Plant Patent No. 1,327).

Subsequent to origination of the variety I asexually reproduced it in my experimental orchard, located as aforesaid, by topworking on mature orchard trees; such reproductions having run true in all respects.

In the drawings:

Fig. 1 is an elevation showing one of the nectarines, together with twigs and leaves.

Fig. 2 is a sectional elevation of one of the nectarines with the stone remaining in place.

Referring to pomological details of this new and distinct variety of nectarine tree and its fruit, the following is an outline description thereof; all major color plate identifications being by reference to Maerz and Paul Dictionary of Color, except where common terms of color definition are employed.

Tree:
- *Size.*—Large to medium.
- *Vigor.*—Vigorous.
- *Production.*—Productive.
- *Bearing.*—Regular bearer.

Trunk: Size—stocky to medium.
Branches: Size—stocky to medium.
Leaves:
- *Size.*—Large to medium.
- *Thickness.*—Thick to medium.
- *Margin.*—Glandular; crenate.
- *Petiole.*—Medium length; medium thickness.
- *Glands.*—Large to medium; reniform. Position—usually two on petiole and two or more on blade.
- *Color.*—Top side—medium green (22–L–6 to 22–L–8). Under side—lighter green (21–K–6).

Flower buds: Size—large to medium.

Flowers: Blooming period (1958).
- *Date of first bloom.*—March 1st.
- *Date of full bloom.*—March 12th. Medium as compared with other varieties.
- *Size.*—Large.
- *Type.*—Showy.

Fruit:
- *Maturity when described.*—Eating ripe—July 3, 1958.
- *Date of first picking.*—June 28, 1958.
- *Date of last picking.*—July 5, 1958.
- *Size.*—Variable. Average diameter axially—2⅝". Average transversely in suture plane—2 7/16".
- *Form.*—Variable; symmetrical; globose to oblong.
- *Suture.*—Distinct; extends from base to apex, with slight depression beyond pistil point.
- *Cavity.*—Rounded.
- *Base.*—Rounded.
- *Apex.*—Short.

Skin:
- *Thickness.*—Thick to medium.
- *Texture.*—Medium.
- *Tendency to crack.*—None noted.
- *Color.*—Yellow (10–L–3) shading to orange-yellow (9–K–8 to 10–L–12), mottled with red (5–L–12).

Flesh:
- *Texture.*—Medium; crisp; melting.
- *Ripens.*—Even.
- *Flavor.*—Subacid; delicate.
- *Eating quality.*—Good.
- *Color.*—Yellow (9–L–2 shading to 9–J–5), with considerable red (3–L–3) adjacent the stone; the surface of the pit cavity being red with yellow fibers.

Stone:
- *Type.*—Free.
- *Size.*—Medium.
- *Form.*—Oblong.
- *Apex.*—Acute.
- *Sides.*—Equal.
- *Ridges.*—Jagged.
- *Pits.*—Elongated.
- *Ventral edge.*—Thin.
- *Dorsal edge.*—Full.
- *Tendency to split.*—Slight.
- *Color.*—Brown (5–A–12).

Use: Market.
Keeping quality: Good.
Shipping quality: Good.

The tree and its fruit herein described may vary in slight detail due to climatic and soil conditions under which the variety may be grown; the present description being of the variety as grown in the Central Valley of California.

The following is claimed:

A new and distinct variety of nectarine tree, as illustrated and described, which bears yellow-fleshed freestone fruit having yellow skin mottled with red; said variety—in comparison with the Sun Grand nectarine—having leaves with reniform instead of globose glands, and bearing fruit which is larger, ripens approximately ten days earlier, and has less red exterior color.

No references cited